United States Patent
Komatsu et al.

(10) Patent No.: US 6,835,320 B1
(45) Date of Patent: Dec. 28, 2004

(54) ZINC-MODIFIED COMPOSITE POLYBASIC SALT, PROCESS FOR PRODUCING THE SAME, AND USE

(75) Inventors: Yoshinobu Komatsu, Chuo-ku (JP); Hitoshi Ishida, Chuo-ku (JP); Hiroshi Igarashi, Chuo-ku (JP); Masami Kondo, Chuo-ku (JP); Madoka Minagawa, Chuo-ku (JP); Tetsu Sato, Chuo-ku (JP); Teiji Sato, Chuo-ku (JP)

(73) Assignee: Mizusawa Industrial Chemicals, Ltd., Tokyo (JP)

( * ) Notice: Subject to any disclaimer, the term of this patent is extended or adjusted under 35 U.S.C. 154(b) by 394 days.

(21) Appl. No.: 09/786,427
(22) PCT Filed: Jul. 7, 2000
(86) PCT No.: PCT/JP00/04555
§ 371 (c)(1), (2), (4) Date: Mar. 6, 2001
(87) PCT Pub. No.: WO01/04054
PCT Pub. Date: Jan. 18, 2001

(30) Foreign Application Priority Data

Jul. 8, 1999 (JP) ............................................ 11/195121

(51) Int. Cl.[7] .................................................. C01F 7/76
(52) U.S. Cl. ........................ 252/62; 423/263; 423/277; 423/306; 423/327.1; 423/326; 423/331; 423/395; 423/420.2; 423/518; 423/463; 556/27; 556/118
(58) Field of Search ................................ 423/593, 600, 423/263, 277, 306, 327.1, 326, 331, 395, 420.2, 518, 463; 252/62; 556/27, 118

(56) References Cited

U.S. PATENT DOCUMENTS 4,454,244 A * 6/1984 Woltermann ................ 423/594
6,071,433 A * 6/2000 Bhattacharyya ............. 423/650

* cited by examiner

Primary Examiner—Wayne A. Langel
(74) Attorney, Agent, or Firm—Sherman & Shalloway

(57) ABSTRACT

A composite metal polybasic salt containing a trivalent metal, zinc metal and a divalent metal as metal components and having a novel crystal structure, and a method of preparing the same. The invention further deals with a composite metal polybasic salt which has anion-exchanging property, which by itself is useful as an anion-exchanger, capable of introducing anions suited for the use upon anion-exchange, and finds a wide range of applications, and a method of preparing the same. The composite metal polybasic salt has a particular chemical composition and X-ray diffraction peaks, exhibiting peaks at $2\theta=2$ to $15°$, $2\theta=19.5$ to $24°$ and $2\theta=33$ to $50°$, and a single peak at $2\theta=60$ to $64°$ in the X-ray diffraction (Cu-α).

11 Claims, 9 Drawing Sheets

RELATIONSHIP BETWEEN THE Zn/Al COMPOSITION RATIO OF THE PRODUCT AND THE SO₃/Al COMPOSITION RATIO OF THE PRODUCT

WAVE NUMBER (cm$^{-1}$)
PBS SERIES IR SPECTRUM (A) Al-Zn TYPE        ANION=$SO_4^{2-}$
(B) Al-Zn-Mg TYPE    ANION=$SO_4^{2-}$
(C) Al-Zn TYPE       ANION=$HPO_4^{2-}$
(D) Al-Zn-Mg TYPE    ANION=$HPO_4^{2-}$
(E) Al-Zn TYPE       ANION=STEARATE
(F) Al-Zn-Mg TYPE    ANION=STEARATE
(G) Al-Zn TYPE       ANION=$Si_2O_7^{2-}$
(H) HYDROTALCITE

X-RAY DIFFRACTION IMAGE OF A COMPOSITE
METAL POLYBASIC SALT PBS (EX.3)

X-RAY DIFFRACTION IMAGE OF A COMPOSITE
METAL POLYBASIC SALT PBS (EX.3)

HIGH-ANGLE SIDE

X-RAY DIFFRACTION IMAGE OF MAGALDRATE

HIGH-ANGLE SIDE

X-RAY DIFFRACTION IMAGE OF USP-REFERRED STANDARD MAGALDRATE

X-RAY DIFFRACTION IMAGE OF
A ZINC-MODIFIED HYDROTALCITE (COMP.EX.2)

X-RAY DIFFRACTION IMAGE OF A SALT OF
LITHIUM ALUMINUM COMPOSITE HYDROXIDE (COMP.EX.3)

HOW TO FIND A LAMINATE ASYMMETRIC INDEX

SCANNING-TYPE ELECTRON MICROPHOTOGRAPH OF EX.3

FIG.10
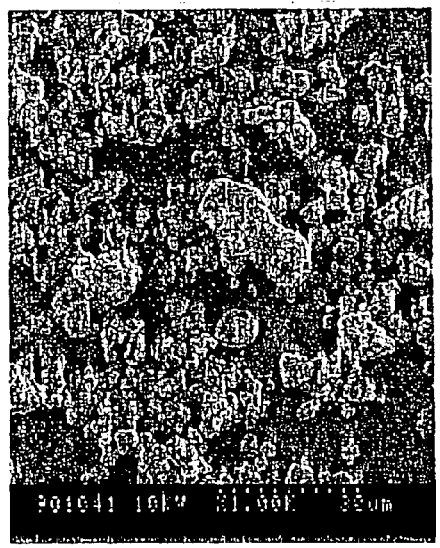 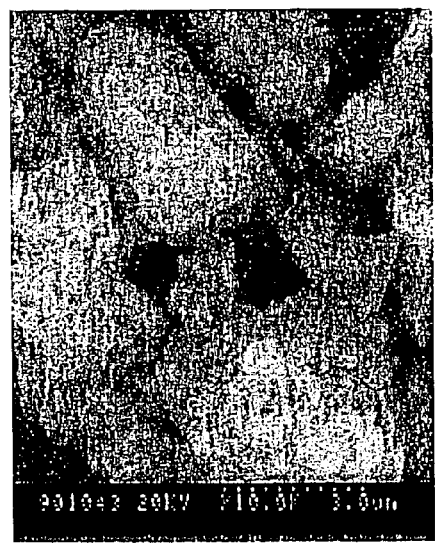
SCANNING-TYPE ELECTRON MICROPHOTOGRAPH OF EX.6
FIG.11
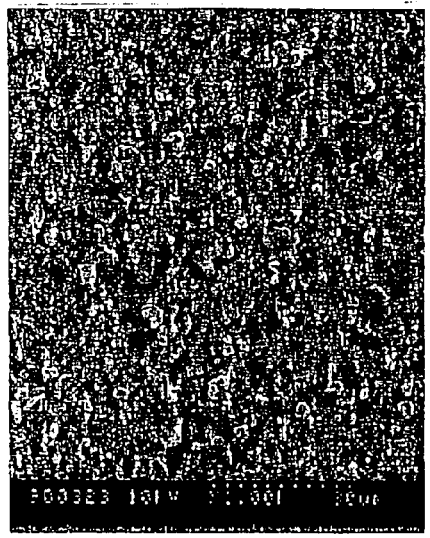 
SCANNING-TYPE ELECTRON MICROPHOTOGRAPH OF EX.7

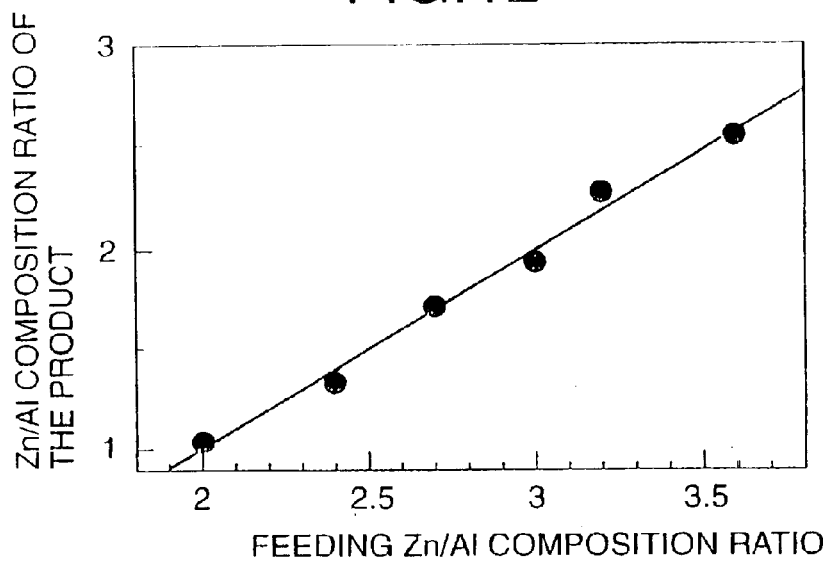
RELATIONSHIP BETWEEN THE FEEDING Zn/Al COMPOSITION RATIO AND THE Zn/Al COMPOSITION RATIO OF THE PRODUCT
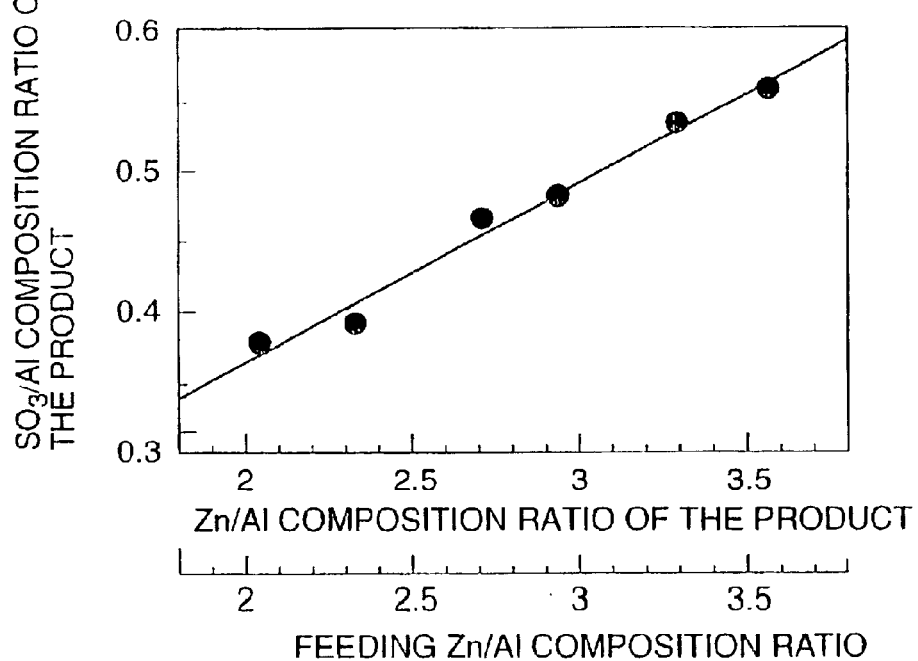
RELATIONSHIP BETWEEN THE Zn/Al COMPOSITION RATIO OF THE PRODUCT AND THE $SO_3$/Al COMPOSITION RATIO OF THE PRODUCT X-RAY DIFFRACTION IMAGE AT THE FEEDING
Zn/Al COMPOSITION RATIOS X-RAY DIFFRACTION IMAGES AT THE Zn/(Zn/+Mg) COMPOSITION RATIOS (FEEDING $M_2$/Al=2.5)

ZINC-MODIFIED COMPOSITE POLYBASIC SALT, PROCESS FOR PRODUCING THE SAME, AND USE

TECHNICAL FIELD

The present invention relates to a composite metal polybasic salt having a novel crystalline structure, a method of preparing the same and use thereof.

BACKGROUND ART

As synthetic composite metal hydroxides, there have heretofore been known a hydrotalcite-type synthetic mineral (e.g., Japanese Examined Patent Publication (Kokoku) No. 32198/1972) and a salt of lithium aluminum composite hydroxide (e.g., Japanese Examined Patent Publication (Kokoku) No. 2858/1995).

There has further been known a polybasic aluminum-magnesium salt. Japanese Examined Patent Publication (Kokoku) No. 38997/1974 teaches a method of producing a is polybasic aluminum salt by reacting a polybasic aluminum sulfate with a magnesium hydroxide at a molar ratio of Al/Mg=1/2 to 4/3 in the presence of water. There has been further stated that the polybasic aluminum magnesium salt can be effectively used as an antacid.

Japanese Unexamined Patent Publication (Kokai) No. 204617/1985 teaches a method of preparing a magaldrate expressed by the formula $Al_5Mg_{10}(OH)_{31}(SO_4)_2 \cdot xH_2O$ by reacting an active aluminum hydroxide with a stoichiometric amount of water-soluble sulfate-containing compound, active magnesium oxide and(or) magnesium hydroxide in the presence of water and, if necessary, drying the resulting magaldrate paste.

Japanese Unexamined Patent Publication (Kokai) No. 102085/1989 discloses a novel aluminum magnesium hydroxy compound represented by the formula $AlxMgy(OH)_{35-z}R_2 \cdot nH_2O$ [wherein R is a residue RCOO- of monocarboxylic acid, and indexes x, y and z satisfy the following conditions $3 \leq x \leq 9$, $4 \leq y \leq 13$, $3 \leq z \leq 5$ and $3x+2y=35$].

Japanese Unexamined Patent Publication (Kokai) No. 164432/1989 discloses an aluminum magnesium hydroxy compound having a layer structure represented by the general formula $AlxMgy(OH)_{35-z}R_2 \cdot nH_2O$ [wherein R is a residue RCOO- of monocarboxylic acid, RCOO- having 2 to 22 carbon atoms, and indexes x, y and z satisfy the following conditions $3 \leq x \leq 9$, $4 \leq y \leq 13$, $3 \leq z \leq 5$ and $3x+2y=35$], and a gel composition containing an oleophilic organic compound which is in the liquid form at room temperature (20° C.).

Japanese Examined Patent Publication (Kokoku) No. 59977/1989 discloses a crystalline basic aluminum magnesium carbonate represented by the formula $Al_2Mg_6(OH)_{12}(CO_3)_2 \cdot xH_2O$ [wherein $x \geq 4$].

Further, Japanese Examined Patent Publication (Kokoku) No. 52409/1991 discloses a method of producing a hydroxyaluminum magnesium sulfate by reacting a solid magnesium hydroxide and/or magnesium oxide with an aqueous solution of aluminum sulfate at an atomic ratio of magnesium:aluminum of from 1:1 to 3:1 until the pH of the reaction mixture becomes 4.0 to 8.0, removing the water-soluble component from the reaction mixture by a known method, followed, if necessary, by drying.

A conventional composite polybasic salt can be represented by a magaldrate comprising aluminum and magnesium. However, the present inventors have succeeded in synthesizing a novel composite metal polybasic salt that has an explicit crystal structure different from those of zinc-modified hydrotalcites.

The inventors have further discovered that the composite metal polybasic salt can be effectively used as an additive for resins, as a heat insulator and as an anion-exchanger.

DISCLOSURE OF THE INVENTION

The object of the present invention is to provide a composite metal polybasic salt containing zinc metal as an essential component and further containing a trivalent metal and a divalent metal (metals other than zinc, the same holds hereinafter), as metal components, and having a novel crystal structure, and a method of preparing the same.

Another object of the present invention is to provide a composite metal polybasic salt which has anion-exchanging property, which by itself is useful as an anion-exchanger, capable of introducing anions suited for the use upon anion-exchange, and finds a wide range of applications, and a method of preparing the same.

According to the present invention, there is provided a composite metal polybasic salt having a chemical composition represented by the following general formula (1),

$$M^2{}_a Zn_b M^3{}_x (OH)_y (A)_z \cdot nH_2O \qquad (1)$$

wherein $M^2$ is a divalent metal other than Zn, $M^3$ is a trivalent metal, A is an inorganic or organic anion, and a, b, x, y and z are numbers satisfying the following formulas, i) $0 \leq a$, $0 < b$
ii) $3x+2(a+b)-y-mz=0$ (wherein m is a valency of anion A),
iii) $0.3 \leq (a+b)/x \leq 2.5$,
iv) $1.5 \leq y/(x+a+b) \leq 3.0$, and
v) $4.0 \leq (x+a+b)/z \leq 20.0$, and
n is a number of not larger than 7, exhibiting diffraction peaks at $2\theta=2$ to $15°$, $2\theta=19.5$ to $24°$ and $2\theta=33$ to $50°$, and a single peak at $2\theta=60$ to $64°$ in the X-ray diffraction (Cu-α).

In the present invention, it is desired that an X-ray diffraction peak at $2\theta=33$ to $50°$ is a single peak.

In the present invention, further, it is desired that the trivalent metal ($M^3$) in the above formula is aluminum, and the divalent metal ($M^2$) in the above formula is magnesium. When $M^2$ is magnesium, it is desired that $(a+b)/x$ is not larger than 2.0. When a is zero, it is allowed that b/x is not larger than 2.5.

In the present invention, it is desired that the anions (A) in the above formula are sulfuric acid ions. The sulfuric acid ions have anion-exchanging property, and can be exchanged with carbonic acid ions, organocarboxylic acid ions, phoshoric acid ions, silicic acid ions (inclusive of condensed silicic acid ions), oxygen acid ions of halogen, aluminic acid ions or sulfonic acid ions.

The composite metal polybasic salt of the present invention exhibits X-ray diffraction peaks at the above-mentioned Bragg angle (irradiation angle theta). For example, the Al—Zn—SO$_4$ composite metal polybasic salt of Example 3 has the following X-ray diffraction image:

| 2 θ | Relative intensity |
| --- | --- |
| 10.97° | 100% |
| 21.03° | 35% |
| 34.27° | 57% |
| 60.97° | 39% |

Among the above X-ray diffraction peaks, a peak at 2θ=33 to 50° is singular, and a laminate asymmetric index (Is) defined by the following formula (2), $$Is = \tan\theta_2 / \tan\theta_1 \quad (2)$$

wherein $\theta_1$ is an angle subtended by a peak perpendicular in the X-ray diffraction peak of a predetermined spacing and a peak tangent on the narrow angle side, and $\theta_2$ is an angle subtended by the peak perpendicular at the above peak and a peak tangent on the wide angle side, is not smaller than 1.5 at a peak of 2θ=33 to 50°.

According to the present invention, there is further provided a method of preparing a composite metal polybasic salt by reacting a water-soluble salt of a trivalent metal with an oxide, a hydroxide or a water-soluble salt of a zinc metal and a divalent metal under the conditions of a pH of from 3.8 to 9.0 and a temperature of not lower than 50 ÅKC and, preferably, not lower than 80° C. and, if necessary, executing the ion exchange in the presence of an acid or a soluble salt of acid.

According to the present invention, further, there is provided an additive for resins, a heat insulator and an anion-exchanger comprising the composite metal polybasic salt.

In the anion-exchanger, it is desired that the anions of the composite metal polybasic salt are sulfuric acid ions.

BRIEF DESCRIPTION OF DRAWINGS

FIG. 10 is a scanning-type electron microphotograph showing the granular structure of the Al—Zn—Mg-type composite metal polybasic salt in which the anions are sulfuric acid ions;

FIG. 11 is a scanning-type electron microphotograph showing the granular structure of the Al—Zn-type composite metal polybasic salt in which the anions are stearic acid ions;

FIG. 12 is a diagram illustrating a relationship between the feeding molar ratio of Zn/M$^{3+}$ in the starting materials and the molar ratio of Zn/M$^{3+}$ in the product in relation to the Al—Zn-type composite metal polybasic salt which is the product of the present invention;

FIG. 13 is a diagram illustrating an increase in the molar ratio of SO$_3$/Al in the product accompanying an increase in the molar ratio of Zn/Al in relation to the Al—Zn-type composite metal polybasic salt which is the product of the present invention;

BEST MODE FOR CARRYING OUT THE INVENTION

Composite Metal Polybasic Salt

Figure 1:
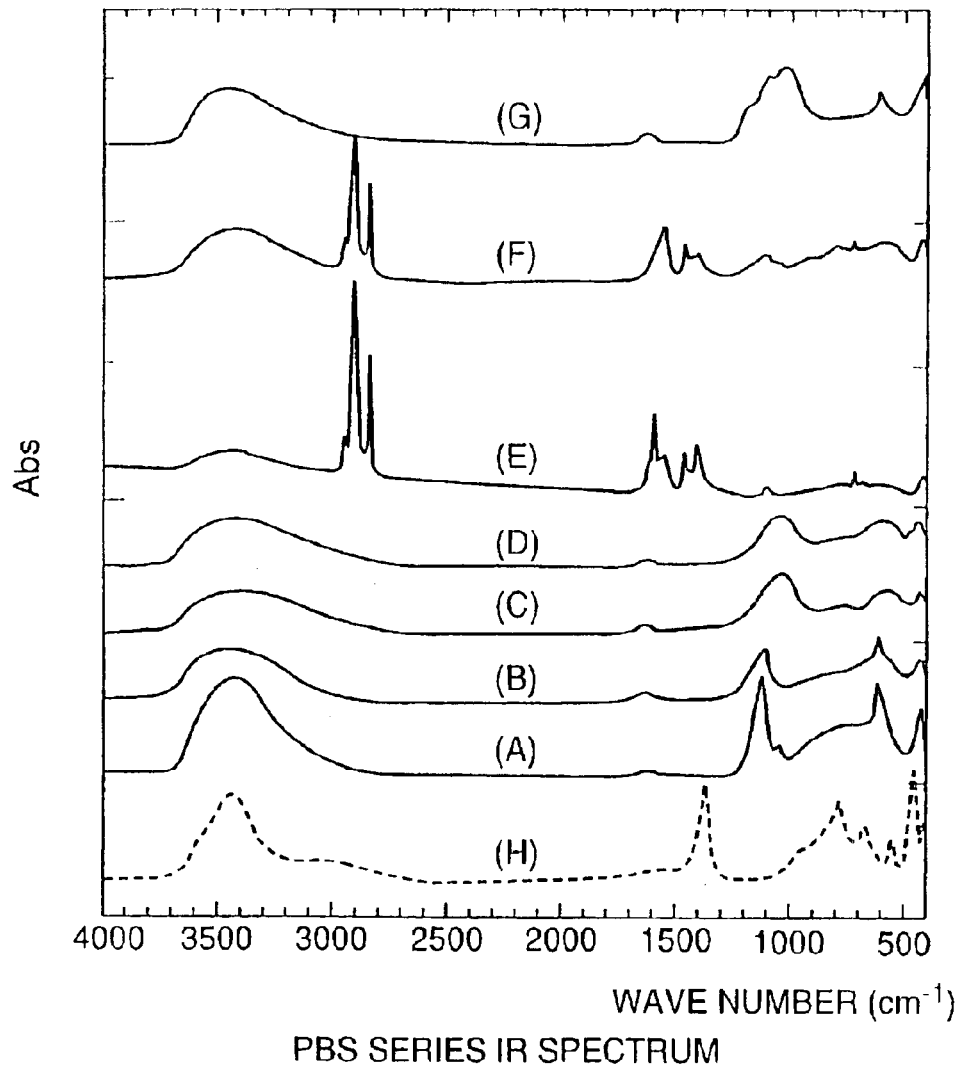
FIG. 1 is a diagram comparing infrared-ray absorption spectra of zinc-modified composite metal polybasic salts which are the products of the present invention with that of a hydrotalcite.

A first feature of the composite metal polybasic salt (hereinafter often referred to as PBS) of the present invention is that it has a chemical composition expressed by the above-mentioned formula (1). That is, the number x of mols of the trivalent metal, the number (a+b) of mols of the divalent metal, the number y of mols of hydroxyl groups and the number z of mols of anions all lie within ranges satisfying the above formulas (i) to (iii).

A hydrotalcite which is a representative example of the known composite metal polybasic salt or of the composite metal hydroxide salt, typically, has a chemical composition expressed by the following formula (4),

$$Mg_6Al_2(OH)_{16}CO_3 \cdot nH_2O \quad (4)$$

and (a+b)/x in the above-mentioned formula (iii) corresponds to 3.0. In the composite metal polybasic salt of the present invention, however, (a+b)/x is not larger than 2.5 and, particularly, not larger than 2.0, and has a chemical composition different from that of the hydrotalcite.

A zinc-modified hydrotalcite has a chemical composition expressed by the following formula (5),

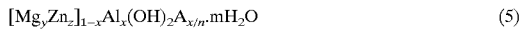
$$[Mg_yZn_z]_{1-x}Al_x(OH)_2 A_{x/n} \cdot mH_2O \quad (5)$$

wherein A is a divalent or a monovalent anion, y, z and x are numbers satisfying the conditions 0.15<z/(y+z)<0.4, 0<x<0.6, n is a valency of anion A, and m is an integer, which is different from the chemical composition of the composite metal polybasic salt of the present invention.

As another example of the composite metal polybasic salt, there has been known a salt of lithium-aluminum composite hydroxide salt represented by the following formula (6),

$[Al_2Li(OH)_6]_n X . mH_2O$          (6).

This compound does not contain a divalent metal but contains a monovalent metal, making a difference from the composite metal polybasic salt of the present invention. Even if two mols of a monovalent metal is equivalent to a mol of a divalent metal, (a+b)/x in the above-mentioned formula (iii) corresponds to 0.25 when X is $CO_3$ or $SO_3$ (n=2). In the composite metal polybasic salt of the present invention, (a+b)/x is not smaller than 0.3 and its chemical composition is also different from that of the known salt of lithium aluminum composite hydroxide.

It is considered that the composite metal polybasic salt of the present invention has the following chemical structure. In this compound, a $[Zn-M^{2+}](OH)_6$ octahedral layer of which $[Zn-M^{2+}]$ is isomorphous-substituted by $M^{3+}$ serves as a basic layer, and anions such as sulfuric acid radicals are incorporated among the basic layers in a form to be balanced with excess of cations due to the substitution. The layered crystal structure is formed by a stack of many basic structures.

Anions such as sulfuric acid radicals present in the composite metal polybasic salt have anion-exchanging property and can be substituted with carbonic acid ions, organocarboxylic acid ions, phosphoric acid ions, silicic acid ions (condensed silicic acid ions), oxygen acid ions of halogen, aluminic acid ions or sulfonic acid ions.

The content Qo (milliequivalent/100 g) of sulfuric acid radicals in the composite metal polybasic salt is from 290 to 270 milliequivalent/100 g.

As the divalent metal $M^{2+}$ constituting the composite metal polybasic salt of the present invention, there can be exemplified Be, Mg, Ca, Ba, Sr, Cd, Mn, Fe, Co, Ni, Cu, Pd, Sn, Pt and Pb. Among them, a metal of the Group II of periodic table and, particular, Mg is preferred.

As the trivalent metal $M^{3+}$ constituting the composite metal polybasic salt, there can be exemplified Al, Sc, Ti, V, Cr, Mn, Fe, Co, Ni, Ga, Y, Ru, Rh, In, Sb, La, Ce, Nd, Pm, Sm, Eu, Gd, Tb, Dy, Ho, Er, Tm, Yb, Lu, Os, Ir, Au, Bi, Ac and Th. Among them, Al is preferred.

As the anions A constituting the composite metal polybasic salt, there can be exemplified inorganic anions and organic anions. As the inorganic anions, there can be exemplified oxygen acid ions such as of S, P, Al, Si, N, B, V, Mn, Mo, W, Cr, Te and Sn, as well as carbonic acid anions.

As the organic anions, there can be exemplified carboxylic acid anions such as of acetic acid, propionic acid, butyric acid, palmitic acid, stearic acid, myristic acid, oleic acid, linolic acid, adipic acid, fumaric acid, maleic acid, citric acid, tartaric acid, malic acid, cyclohexanecarboxylic acid, benzoic acid, salicylic acid, phthalic acid and terephthalic acid; sulfonic acid ions such as of methane sulfonic acid, toluene sulfonic acid, lignin sulfonic acid and dodecylbenzene sulfonic acid; aromatic primary amines such as sulfanilic acid, aniline, o-toluidine, m-toluidine, metanilic acid and benzylamine as well as hydrochloric acid, nitric acid, sulfuric acid, phosphoric acid, hydrobromic acid and hydrofluoric acid thereof.

FIG. 1 in the accompanying drawings shows infrared-ray absorption spectra of the composite metal polybasic salts of the present invention in comparison with the infrared-ray absorption spectrum of a hydrotalcite.

That is, FIG. 1(A) is an infrared-ray absorption spectrum of an Al—Zn-type composite metal polybasic salt in which the anions are sulfuric acid ions, FIG. 1(B) is an infrared-ray absorption spectrum of an Al—Zn—Mg-type composite metal polybasic salt in which the anions are sulfuric acid ions, FIG. 1(C) is an infrared-ray absorption spectrum of an Al—Zn-type composite metal polybasic salt in which the anions are monohydrogen phosphoric acid ions, FIG. 1(D) is an infrared-ray absorption spectrum of an Al—Zn—Mg-type composite metal polybasic salt in which the anions are monohydrogen phosphoric acid ions, FIG. 1(E) is an infrared-ray absorption spectrum of an Al—Zn-type composite metal polybasic salt in which the anions are stearic acid ions, FIG. 1(F) is an infrared-ray absorption spectrum of an Al—Zn—Mg-type composite metal polybasic salt in which the anions are stearic acid ions, FIG. 1(G) is an infrared-ray absorption spectrum of an Al—Zn-type composite metal polybasic salt in which the anions are silicic acid ions, and FIG. 1(H) is an infrared-ray absorption spectrum of a hydrotalcite in which the anions are carbonic acid ions.

From these infrared-ray absorption spectra, it is learned that the composite metal polybasic salts of the present invention exhibit characteristic absorptions due to the hydroxyl group at wave numbers of from 3800 to 2700 $cm^{-1}$ and characteristic absorptions due to the incorporated anions at wave numbers of from 900 to 1500 $cm^{-1}$. In particular, the composite metal polybasic salts of the present invention exhibit sharp absorption peaks in the far infrared regions of a wave number of not larger than 2000 $cm^{-1}$, and are useful as a heat insulator for absorbing heat rays.

Further, the Al—Zn-type composite metal polybasic salt in which the anions are stearic acid ions, exhibits characteristic absorptions due to the methylene group at wave numbers of from 3000 to 2800 $cm^{-1}$ and characteristic absorptions due to carboxylate ions at wave numbers of from 1650 to 1500 $cm^{-1}$.

The composite metal polybasic salt (PBS) of the present invention has a novel crystal structure which is quite different from those of the hydrotalcite and a salt of lithium aluminum composite hydroxide.

Figure 2:
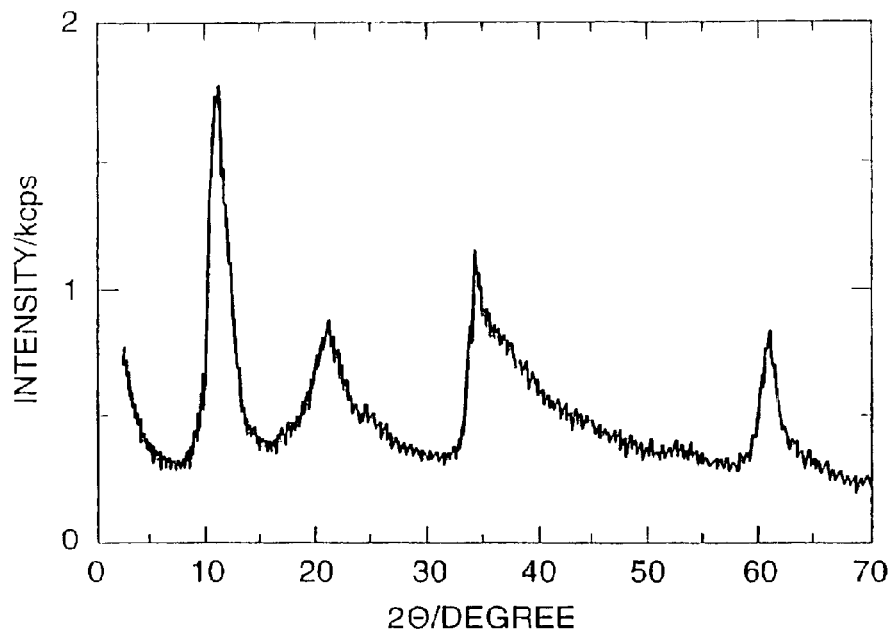
FIG. 2 is a diagram illustrating an X-ray diffraction image of an Al—Zn-type composite metal polybasic salt of the present invention.
Figure 3:
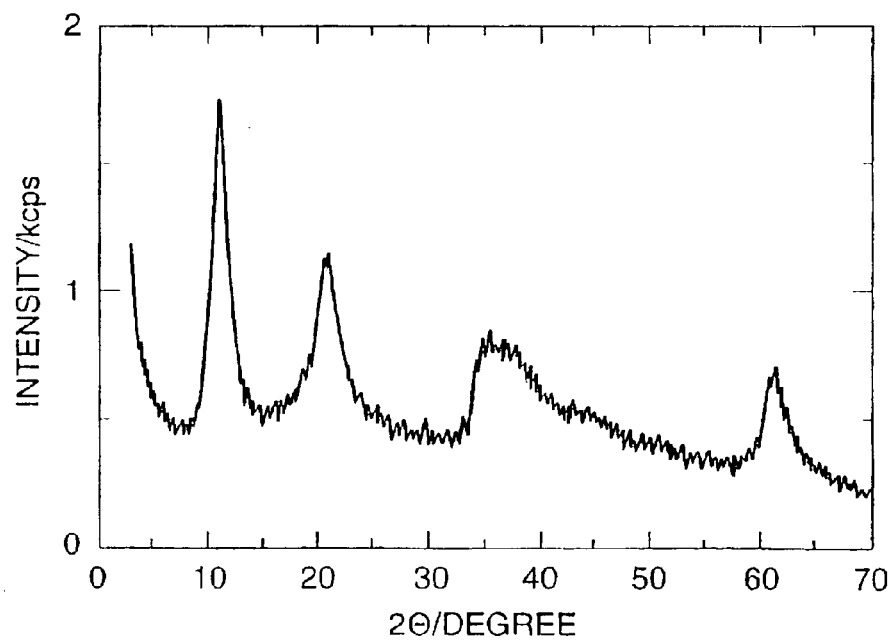
FIG. 3 is a diagram illustrating an X-ray diffraction image of an Al—Zn—Mg-type composite metal polybasic salt of the present invention.

FIG. 2 in the attached drawings shows an X-ray diffraction image of the PBS of the Al—Zn type according to the present invention, and FIG. 3 shows an X-ray diffraction image of the PBS of the Al—Zn—Mg type according to the present invention.

Figure 4:
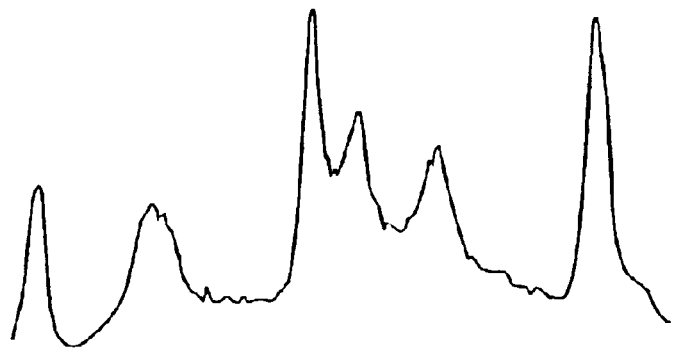
FIG. 4 is a diagram illustrating an X-ray diffraction image of a known magaldrate.
Figure 5:
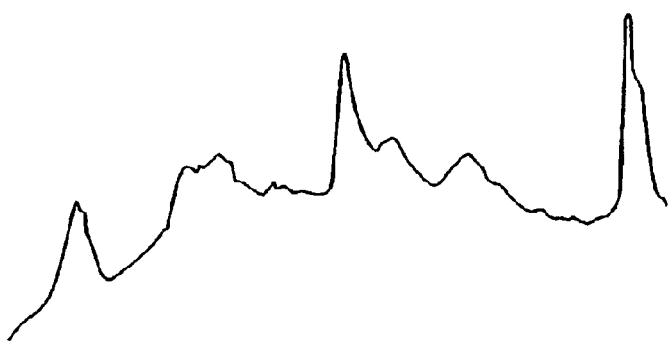
FIG. 5 is a diagram illustrating an X-ray diffraction image of a USP standard magaldrate.
Figure 6:
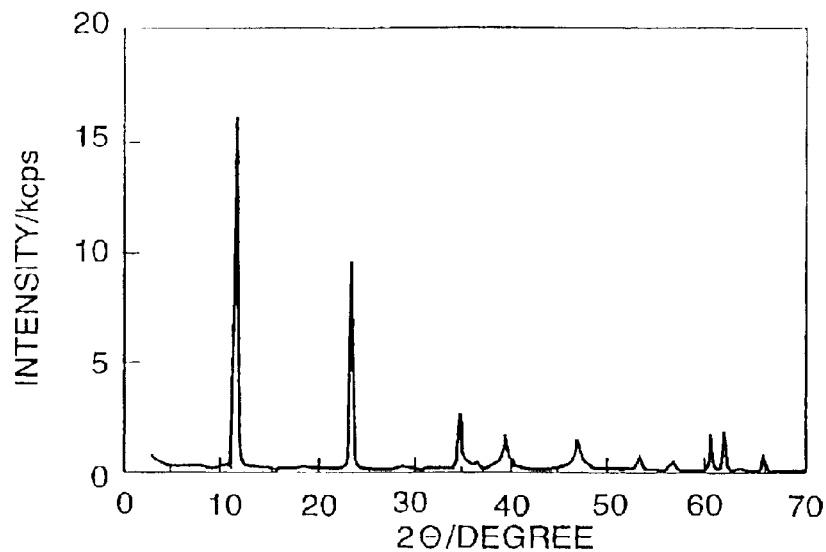
FIG. 6 is a diagram illustrating an X-ray diffraction image of a Zn-type hydrotalcite.
Figure 7:
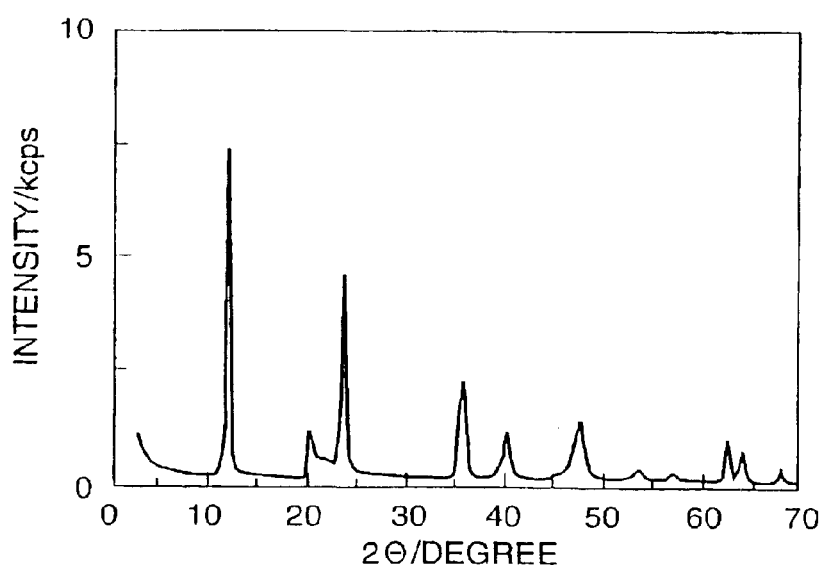
FIG. 7 is a diagram illustrating an X-ray diffraction image of a salt of lithium aluminum composite hydroxide.

FIGS. 4 and 5 are diagrams of X-ray diffraction images of known magaldrates, FIG. 6 is a diagram of an X-ray diffraction image of a zinc-type hydrotalcite, and FIG. 7 is a diagram of an X-ray diffraction image of a salt of lithium aluminum composite hydroxide.

The composite metal polybasic salt of the present invention in which the anions are sulfuric acid ions exhibits substantially four diffraction peaks in the X-ray diffraction (Cu-α) at 2θ=10 to 12°, 2θ=20 to 22°, 2θ=33 to 50° and 2θ=60 to 64°, the diffraction peak at 2θ=60 to 64° being a single peak and, preferably, the diffraction peak at 2θ=33 to 50° being a single peak, too.

On the other hand, the hydrotalcite (FIG. 6) exhibits two diffraction peaks in the range of 2θ=38 to 50°, and another two diffraction peaks in the range of 2θ=60 to 63°. Thus, the above two compounds exhibit quite different X-ray diffraction images.

Further, the known magaldrate exhibits diffraction peaks at 2θ=10 to 12°, 2θ=22 to 24°, 2θ=33 to 35°, 2θ=38 to 40°, 2θ=45 to 47° and 2θ=60 to 64°. Thus, the two compounds exhibit quite different X-ray diffraction images.

Similar differences are also recognized even in the case of a salt of lithium aluminum composite hydroxide (FIG. 7).

From the diffraction peaks of the X-ray diffraction images of the plane (001) at 2θ=10 to 12° of the composite metal polybasic salt of the present invention and the magaldrate, further, it will be leaned that the crystals of the composite metal polybasic salt of the invention are developing in the direction of the C-axis. Further, the composite metal polybasic salt which is a product of the present invention has a degree of orientation ($I_O$) represented by the following formula (3), $$I_O = I_{11}/I_{61} \quad (2)$$

wherein $I_{11}$ is an X-ray diffraction peak intensity at 2θ=10 to 12°, and $I_{61}$ is an X-ray diffraction peak intensity at 2θ=60 to 64°, of larger than 2, which is quite different from that of the known magaldrate ($I_O<1$). From this fact, the composite metal polybasic salt which is a product of the present invention has a large particle composed of primary particles that are expanding in the direction of AB-axis. The primary particle is composed of the basic layer. Accordingly, the product of the present invention disperses well in the resin making it possible to strikingly improve transparency of the blended resin, chlorine-trapping property, resistance against acid and heat resistance.

Figure 8:
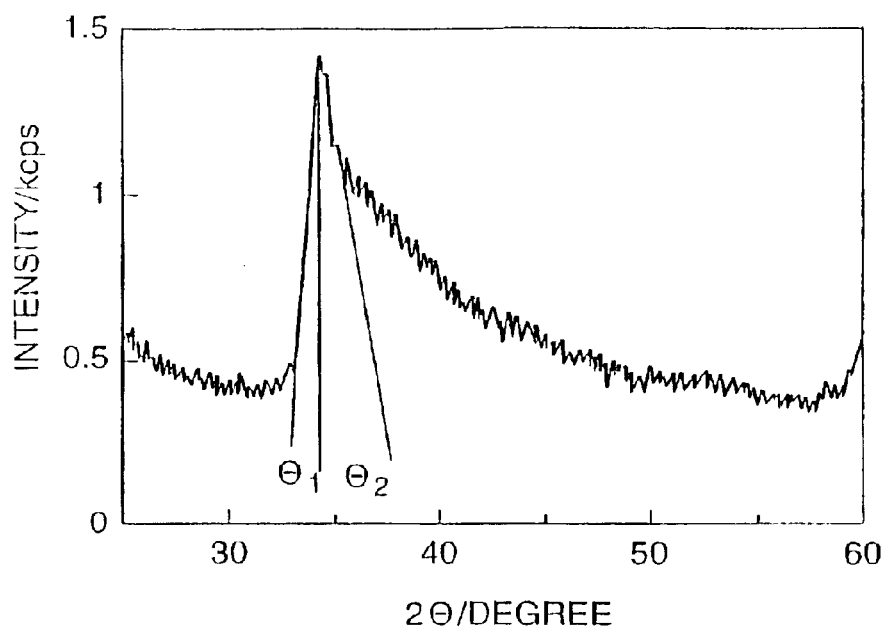
FIG. 8 is a diagram illustrating how to find a laminate asymmetric index.

As will be obvious from FIG. 8, further, the composite metal polybasic salt of the present invention has a feature in the X-ray diffractive fine structure called laminate asymmetry.

That is, it is obvious that the diffraction peak at 2θ=33 to 50° exhibited by the composite metal polybasic salt of the present invention is an asymmetric peak.

In other words, it will be understood that the asymmetric peak rises relatively sharply on the narrow angle side (side on where 2θ is small) and is mildly inclined on the wide angle side (side on where 2θ is large). The asymmetric peak becomes conspicuous particularly at 2θ=33 to 50°. Asymmetry similarly appears even at a peak of 2θ=60 to 64° though the degree of asymmetry is small.

In this specification, the laminate asymmetric index (Is) is defined as described below. That is, an X-ray diffraction chart shown in FIG. 8 is obtained by a method described in an Example appearing later. A maximum inclination peak tangent a on the narrow angle side and a maximum inclination peak tangent b on the broad angle side, are drawn on a peak at 2θ=33 to 50°, and a perpendicular c is drawn from a point where the tangent a intersects the tangent b. Next, an angle θ1 subtended by the tangent a and the perpendicular c, and an angle θ2 subtended by the tangent b and the perpendicular c, are found. The laminate asymmetric index (Is) is found from these angles in compliance with the above formula (2).

The laminate asymmetric index (Is) is 1.0 when the peak is completely symmetrical, and increases as the breaking angle becomes larger than the rising angle.

The laminate asymmetric index (Is) has the following meaning. It was pointed out already that the PBS of the present invention has a laminar crystal structure in which basic layers of $M^2_a Zn_b M^3_x(OH)_y$ are stacked one upon the other. However, it is believed that the sizes (lengths and areas) of the basic layers are not uniform but are varying over wide ranges and, besides, the basic layers are twisted or curved forming a structure which is not plane.

In the PBS of the present invention, therefore, the anions easily exchange ions offering a large ion-exchange capacity and a large ion-exchange rate. When this is used as an additive for a resin for trapping, for example, chlorine ions, then, an excellent ability is exhibited.

When heated from room temperature up to a temperature of 200° C., the composite metal polybasic salt of the present invention exhibits a weight reduction ratio of not larger than 15% by weight and, particularly, not larger than 5% by weight, and offers a distinguished advantage that it does not develop foaming at a resin-working temperature when it is mixed into the resin. The hydrotalcite has a defect of developing foaming as the water separates at the resin-working temperature. The composite metal polybasic salt of the present invention is free from this problem.

The hydrotalcite exhibits a very large endothermic peak due to the vaporization of water in a temperature range of from 190 to 240° C., whereas the PBS does not exhibit such a large endothermic peak proving its excellent resistance against the foaming.

The composite metal polybasic salt of the present invention varies the surface area to a large extent depending upon the kind of anions to be exchanged, and, for example, possesses a small specific surface area and a small porous volume when the anions are sulfuric acid ions. In this case, the PBS of the present invention has a BET specific surface area of not larger than 10 m$^2$/g and, particularly, in a range of from 0.3 to 7 m$^2$/g, and a porous volume of those pores having diameters of from 17 to 3000 angstroms as found by the BJH method of from 0.0005 to 0.05 ml/g and, particularly, from 0.02 to 0.035 ml/g. When the anions are silicic acid ions, on the other hand, the PBS of the present invention has a large specific surface area and a large porous volume, e.g., has the BET specific surface area of about 150 m$^2$/g and the porous volume of those pores having diameters of from 17 to 3000 angstroms of about 0.4 ml/g as found by the BJH method.

The composite metal polybasic salt of the present invention has a volume based median diameter ($D_{50}$) of, generally, from 0.1 to 50 μm and, particularly, from 2 to 10 μm as measured by the laser diffraction method.

The particles have various shapes ranging from a plate-like crystalline particulate shape to an agglomerated shape depending upon the kind of divalent metal $M^{2+}$ of the composite metal polybasic salt.

Figure 9:
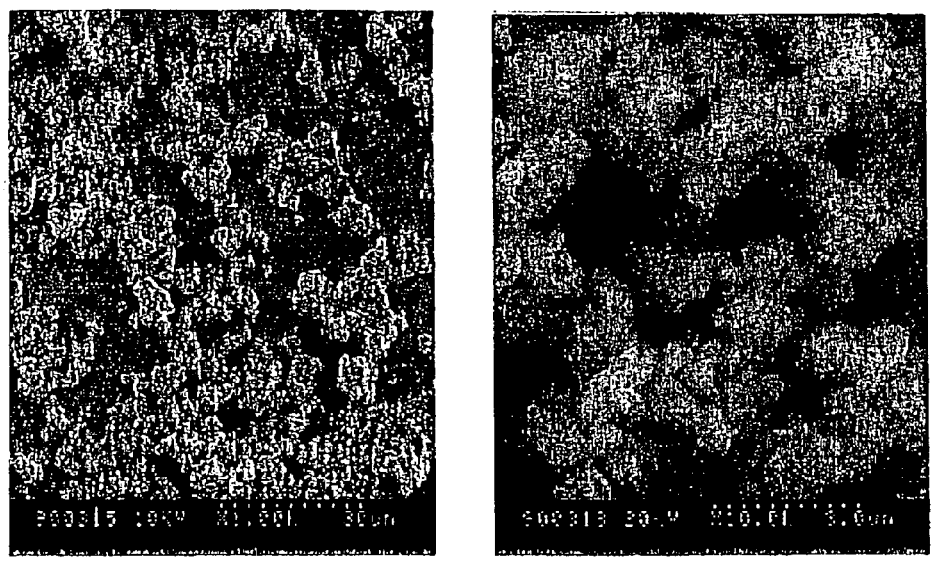
FIG. 9 is a scanning-type electron microphotograph showing the granular structure of the Al—Zn-type composite metal polybasic salt in which the anions are sulfuric acid ions.

FIGS. 9 and 10 are scanning-type electron microphotographs showing the granular structures of an Al—Zn-type composite metal polybasic salt and of an Al—Zn—Mg-type composite metal polybasic salt in which the anions are sulfuric acid ions, and FIG. 11 is a scanning-type electron microphotograph showing the granular structure of an Al—Zn-type composite metal polybasic salt in which the anions are stearic acid ions.

From these photographs, the Al—Zn-type composite metal polybasic salt comprises primary particles which are plate-like crystalline particles.

Method of Preparation

According to the present invention, the composite metal polybasic salt is prepared by reacting a water-soluble salt of a trivalent metal with an oxide, a hydroxide or a water-soluble salt of zinc alone or of zinc and a divalent metal under the conditions of a pH of from 3.8 to 9.0 and a temperature of not lower than 50° C. and, if necessary, executing the ion exchange in the presence of an acid or a soluble salt of acid.

As the water-soluble salt of a trivalent metal such as Al or the like, there can be used any one of a chloride, a nitrate or a sulfate that is soluble in water. From the standpoint of easy synthesis, however, it is desired in the present invention to synthesize the composite metal polybasic salt in the form of a sulfate. It is therefore most desired to use the composite metal polybasic salt in the form of a sulfate.

The starting Zn and divalent metal can be used in any form of an oxide, a hydroxide or a water-soluble salt. From the standpoint of synthesis, however, it is most convenient to use an oxide such as zinc flower or a hydroxide such as magnesium hydroxide. Even when a water-soluble salt such as a chloride, a nitrate or a sulfate of zinc and a divalent metal is used, it is possible to synthesize a composite metal polybasic salt according to the present invention by controlling the pH in the control system to lie within the above-mentioned range, as a matter of course.

In the present invention, it is important to carry out the reaction of the above-mentioned starting materials while maintaining the pH at the time when the reaction is finished to lie within a range of from 3.8 to 9.0 and, particularly, from 4.0 to 8.0, and maintaining the reaction temperature to be not lower than 50° C. and, particularly, from 80 to 180° C.

When the pH of the reaction system lies outside the above range, it becomes difficult to form the composite metal polybasic salt. That is, the composite metal polybasic salt has a feature in that it possesses both the hydroxyl group and the anionic group that are bonded. When the pH becomes larger than the above range, it becomes difficult to introduce the anionic group. When the pH becomes smaller than the above range, on the other hand, it becomes difficult to introduce the hydroxyl group.

When the temperature becomes lower than the above-mentioned range, it becomes difficult to synthesize the composite metal polybasic salt.

The reacting and mixing ratio of the trivalent metal compound and zinc alone or zinc and the divalent metal compound is so set that the composition ratio of the above-mentioned general formula (1) is satisfied. In general, the molar ratio of $(Zn+M^{2+})/M^{3+}$ in the product tends to become smaller than the feeding molar ratio of $(Zn+M^{2+})/M^{3+}$ in the starting material.

FIG. 12 in the accompanying drawing illustrates a relationship between the feeding molar ratio of Zn/Al in the starting material and the molar ratio of Zn/Al in the product in relation to the Al—Zn-type composite metal polybasic salt. The relationship between the two is almost linear, from which it will be understood that the molar ratio of Zn/Al in the final product can be determined by determining the feeding molar ratio.

When ZnO is used as the starting $M^2$ material and $Al_2(SO_4)_3$ is used as a starting $M^3$ material, it is desired that the feeding molar ratio of $Zn/M^{3+}$ is in a range of from 2.0 to 4.0 and, particularly, from 2.0 to 3.6.

There also exists a predetermined relationship among the feeding molar ratio of $Zn/M^{3+}$ in the starting material, the molar ratio of $Zn/M^{3+}$ in the product and the molar ratio of $A/M^{3+}$ in the product. In general, the molar ratio of $A/M^{3+}$ in the product increases with an increase in the molar ratio of $Zn/M^{3+}$.

FIG. 13 illustrates a relationship between the above two, from which it will be learned that the molar ratio of $SO_3/Al$ in the product monotonously increases with an increase in the molar ratio of Zn/Al.

This phenomenon is considered to be as described below.

It was pointed out already that in the PBS of the present invention, a $[Zn–M^{2+}](OH)_6$ octahedral layer of which $[Zn–M^{2+}]$ is isomorphous-substituted by $M^{3+}$ serves as a basic layer, and anions such as sulfuric acid radicals are incorporated among the basic layers in a form to be balanced with excess of cations due to the substitution. When the sulfuric acid radicals are all incorporated in a form to be balanced by excess of cations, the molar ratio of $SO_3/Al$ becomes 0.5. Therefore, the fact of FIG. 13 tells that in a state where the molar ratio of Al is small, nearly ideal state holds. However, as the molar ratio of Al increases, the degree of incorporation of the sulfuric acid radicals decreases and the bonds with the hydroxyl groups increase.

Figure 14:
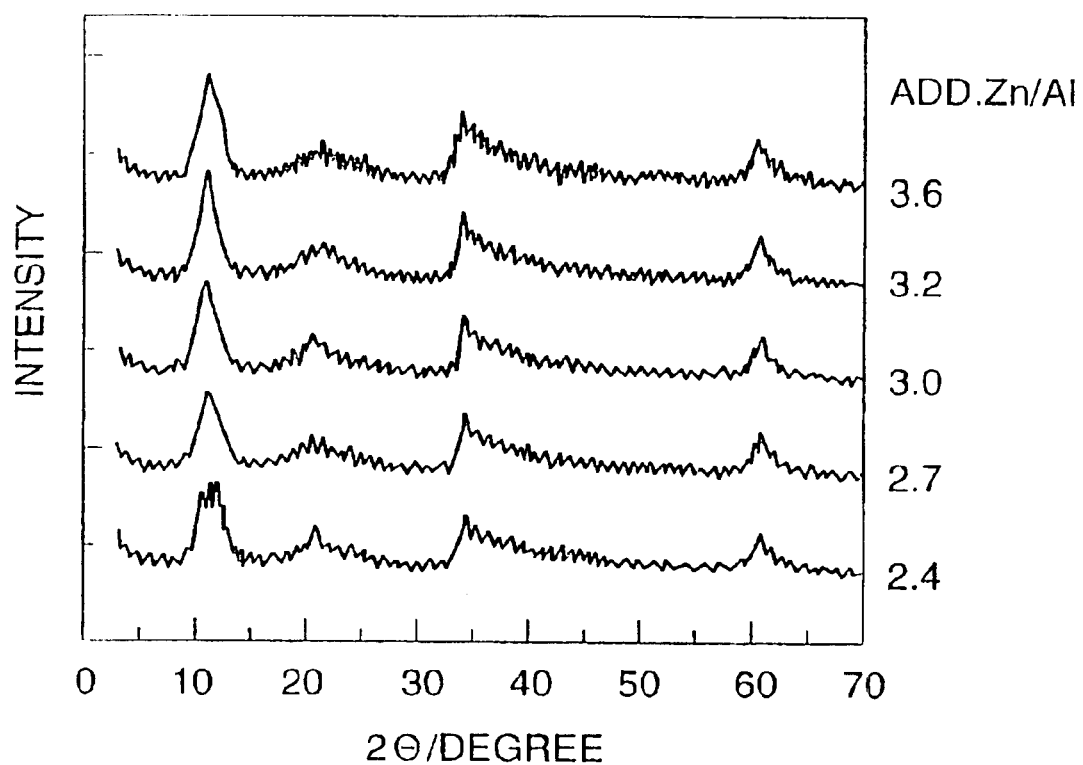
FIG. 14 is a diagram illustrating X-ray diffraction images of a product of when the feeding molar ratio Zn/Al of starting materials is changed in relation to the Al—Zn-type composite metal polybasic salt which is the product of the present invention.

FIG. 14 shows an X-ray diffraction image of a product of when the feeding molar ratio Zn/Al of the starting material is changed in relation to the Al—Zn composite metal polybasic salt. These results tell that the crystal structure of the present invention is stably formed when the molar ratio of Zn/Al lies within a range of from 2.4 to 3.6.

Figure 15:
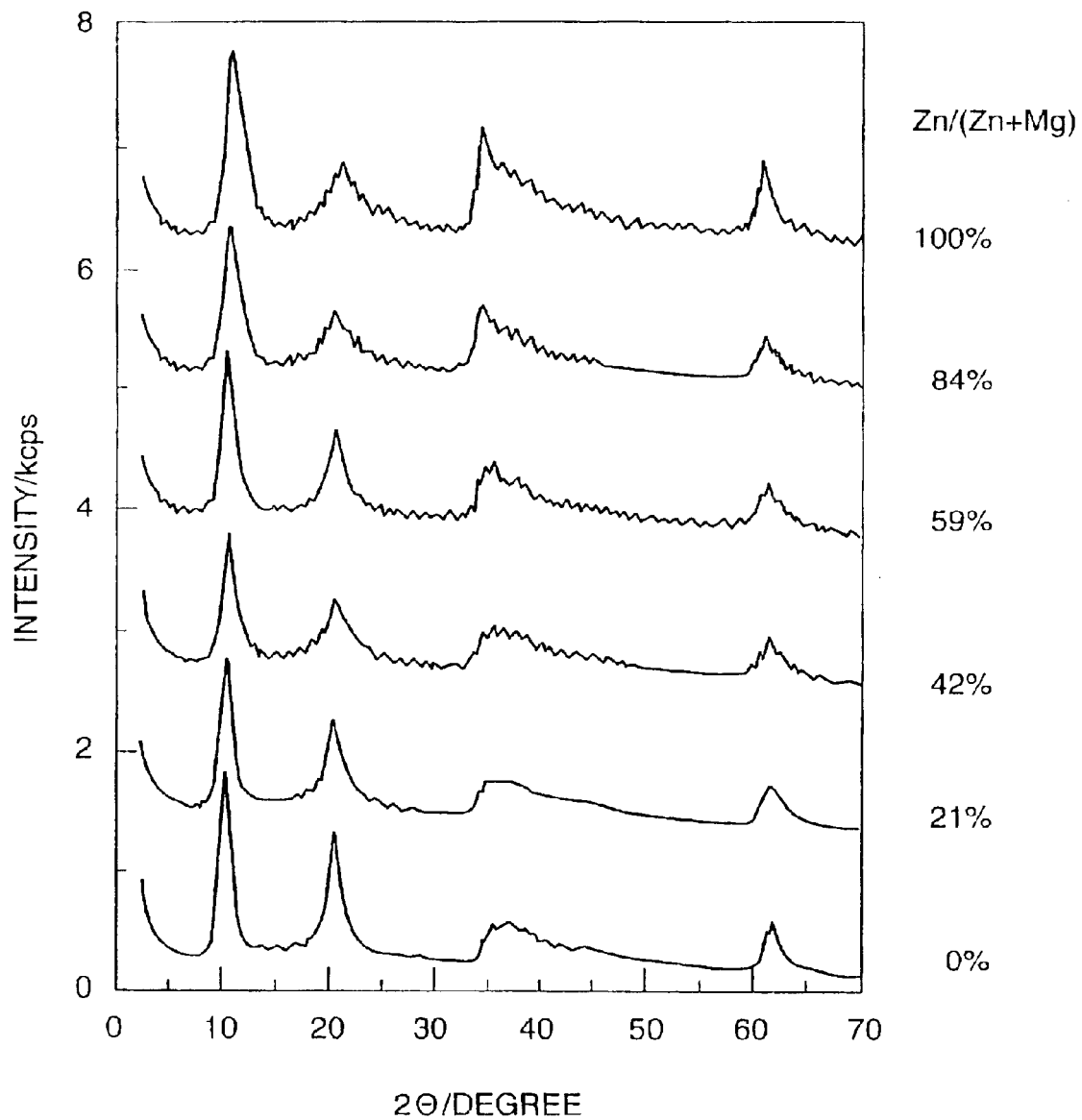
FIG. 15 is a diagram illustrating X-ray diffraction images of a product of when the feeding molar ratio Zn/(Zn+Mg) of starting materials is changed in relation to the Al—Zn—Mg-type composite metal polybasic salt which is the product of the present invention.

FIG. 15 shows an X-ray diffraction image of the Al—Zn—Mg composite polybasic salt of when the molar ratio Zn/(Zn+Mg) of the product is changed. These results tell that the crystal structure of the present invention is stably formed within a range of 0<Zn/(Zn+Mg) mol %≦100.

In synthesizing the composite metal polybasic salt of the present invention, there is no particular limitation on the order of mixing the two starting materials. For example, an aqueous solution or slurry of an oxide of zinc alone or of zinc and a divalent metal, of a hydroxide thereof or of water-soluble salts thereof may be added to an aqueous solution of trivalent metal salts. Conversely, an aqueous solution of trivalent metal salts may be added to an aqueous solution or slurry of an oxide of zinc alone or of zinc and a divalent metal, of a hydroxide thereof or of water-soluble salts thereof, or they may be simultaneously added together.

The reaction can be completed by maintaining the reaction mixture at the above-mentioned temperature for about 2 to 72 hours with stirring. Though not generally required, the reaction may be conducted under the hydrothermal conditions by using a pressurized container. The reaction product is washed with water, subjected to the solid-liquid separation operation such as filtration, dried at 60 to 150° C., and, if necessary, is heat-treated at 150 to 230° C. to obtain a product.

In the composite metal polybasic salt of the present invention, a variety of anions can be introduced by the ion-exchange method. As the starting composite metal polybasic salt to be used for the anion-exchange, it is desired to use the composite metal polybasic salt of the sulfuric acid type.

As the anions to be subjected to the ion-exchange, there is used an alkali metal salt such as sodium salts of the above-mentioned anions. For example, a sodium bicarbonate or a sodium carbonate is used for introducing carboxylic acid radicals, a sodium carboxylate or a sodium sulfonate is used for introducing organic acid anions, a sodium phosphate, a monohydrogen sodium phosphate or a dihydrogen sodium phosphate is used for introducing phosphoric acid radicals, and a sodium silicate is used for introducing silicic acid radicals, to which only, however, the invention is in no way limited.

Anions based on the ion exchange can be introduced by bringing a composite metal polybasic salt of the sulfuric acid type in the form of a powder or a wet cake into uniform contact with an aqueous solution of a salt of the above-mentioned anions at a temperature of from 0 to 100° C. In general, the ion-exchange processing is completed by executing the contact for from about 5 minutes to about 3 hours.

The obtained product is subjected to the filtration, washing with water, drying and, if necessary, to the pulverization and classification to obtain a product.

The composite metal polybasic salt of the present invention can be used in its own form as an additive for resins, as an anion-exchanger or as a heat insulator. If necessary, however, it may be coated with an organic assistant or an inorganic assistant and can, then, be used for a variety of applications.

As the organic assistant, there can be exemplified such coating agents as metal soaps such as calcium salt, zinc salt, magnesium salt and barium salt of stearic acid, palmitic acid or lauric acid; silane coupling agent, aluminum coupling agent, titanium coupling agent, zirconium coupling agent, various waxes, and unmodified or modified resins (e.g., rosin, petroleum resin, etc.). The composite metal polybasic salt of the present invention can be treated for its surfaces with the above coating agent and can be used for a variety of applications.

It is desired to use the coating agent in an amount of from 0.5 to 10% by weight and, particularly, from 1 to 5% by weight with respect to the PBS.

As the inorganic assistant, there can be exemplified regular particles of fine particulate silica such as aerosil and hydrophobically treated aerosil, silicates such as calcium silicate and magnesium silicate, metal oxides such as calcia, magnesia and titania, metal hydroxide such as magnesium hydroxide and aluminum hydroxide, metal carbonates such as calcium carbonate, synthetic zeolites of the A-type, P-type, etc, and acid-treated products thereof or metal ion-exchanged product thereof, with which the PBS can be blended or sprinkled.

It is desired to use these inorganic assistants in an amount of from 0.01 to 200% by weight and, particularly, from 0.1 to 100% by weight per the PBS.

As additives, there may be further blended urea, ethyleneurea, propyleneurea, 5-hydroxypropyleneurea, 5-methoxypropyleneurea, 5-methylpropyleneurea, parabanic acid, 4,5-dimethoxyethyleneurea, pyrrolidene, piperidine, morpholine, dicyandianlide, 2-hydrazobenzothiazole, potassium permanganate, benzalkonium chloride, iodophor, hydrazine, hydrazine sulfate, aluminum sulfate hydrazine sulfate complex salt, organic/inorganic antibacterial agent (iodophor and silver-exchanged zeolite), and optical catalyst (anatase-type titanium oxide, etc.).

Use

The PBS of the present invention has excellent properties as described above. By utilizing these properties, the PBS can be used in such applications as an additive for resins, an ion (anion)-exchanger, a heat insulator, a base member for cosmetics, a de-odoring/antibacterial agent, a flame retardant, an ultraviolet ray-absorbing agent, a nanocomposite starting material, etc.

The composite metal polybasic salt of the present invention is useful as an additive for thermoplastic resins, thermosetting resins and various rubbers.

That is, the composite metal polybasic salt of the present invention does not develop foaming that is caused when the water separates at the resin-working temperature, can be easily blended in the resin, and exhibits excellent heat stability since it contains components such as zinc alone or zinc and divalent metals, trivalent metal components and hydroxyl groups that impart heat-stabilizing property to the resins. Besides, the composite metal polybasic salt has anion-exchanging property and exhibits excellent property for trapping chlorine ions. Moreover, the composite metal polybasic salt absorbs far infrared rays and exhibits excellent heat-retaining property.

Besides, the product of the invention containing zinc exhibits excellent antibacterial property and de-odoring property.

Thus, the composite metal polybasic salt of the present invention can be blended in the resins as a heat stabilizer,.as a halogen catcher, as a heat-retaining agent, as an antibacterial agent, as a de-odoring agent or as an anti-blocking agent.

As the thermoplastic resin to be blended with the composite metal polybasic salt of the present invention, there can be preferably exemplified an olefin resin and, particularly, a low-, an intermediate- or a high-density polyethylene, an isotactic polypropylene, a syndiotactic polypropylene, or a polypropylene polymer which is a copolymer thereof with an ethylene or an a-olefin, a linear low-density polyethylene, an ethylene/propylene copolymer, a polybutene-1, an ethylene/butene-1 copolymer, a propylene/butene-1 copolymer, an ethylene/propylene/butene-1 copolymer, an ethylene/vinyl acetate copolymer, an ionically crosslinked olefin copolymer (ionomer), or an ethylene/acrylic acid ester copolymer, which may be used in a single kind or being blended in two or more kinds.

The additive for resins of the present invention can also be used for other known resin films, fibers and resin-molded articles, such as polyamides like nylon 6, nylon 6-6, nylon 6-10, nylon 11 and nylon 12, thermoplastic polyesters such as polyethylene terephthalate and polybutylene terephthalate, as well as polycarbonate, polysulfone, vinyl chloride resin, vinylidene chloride resin and vinyl fluoride resin.

When used as a blending agent for resins, it is desired that the composite metal polybasic salt is used in an amount of from 0.01 to 200 parts by weight and, particularly, in an amount of from 0.1 to 100 parts by weight per 100 parts by weight of the thermoplastic resin.

The thermoplastic resins, various rubbers and thermosetting resins can be blended with the composite metal polybasic salt of the present invention as an additive for modifying the resins.

As the elastomer polymer for rubbers, there can be exemplified a nitrile-butadiene rubber (NBR), a styrene-butadiene rubber (SBR), a chloroprene rubber (CR), a polybutadiene (BR), a polyisoprene (PI), a butyl rubber, a natural rubber, an ethylene-propylene rubber (EPR), an ethylene-propylene-diene rubber (EPDM), a polyurethane, a silicone rubber and an acrylic rubber. As the thermoplastic elastomer, there can be exemplified a styrene-butadiene-styrene block copolymer, a styrene-isoprene-styrene block copolymer, a hydrogenated styrene-butadiene-styrene block copolymer, a hydrogenated styrene-isoprene-styrene block copolymer, and a partially crosslinked olefinic thermoplastic elastomer.

As the thermosetting resin, there can be exemplified a phenol-formaldehyde resin, a furan-formaldehyde resin, a xylene-formaldehyde resin, a ketone-formaldehyde resin, a urea-formaldehyde resin, a melamine-formaldehyde resin, an alkyd resin, an unsaturated polyester resin, an epoxy resin, a bismaleimide resin, a triallylcyanulate resin, a thermosetting acrylic resin and a silicone resin, which may be used in a combination of two or more kinds.

In this case, the composite metal polybasic salt of the present invention is used in an amount of from 0.01 to 200 parts by weight and, particularly, in an amount of from 0.1 to 100 parts by weight per 100 parts by weight of the thermoplastic resin, thermosetting resin or elastomer.

EXAMPLES

The present invention will now be described by way of Examples to which only, however, the present invention is in no way limited. The testing was conducted in compliance with the following methods.

(1) X-ray Diffraction Measurement.

Measured for Cu—Kα by using a RAD-IB system manufactured by Rigaku Denki Co.

| Target | Cu |
| --- | --- |
| Filter | curved crystalline graphite monochrometer |
| Detector | SC |
| Voltage | 40 KVP |
| Current | 20 mA |
| Count full-scale | 700 c/s |
| Smoothing point | 25 |
| Scanning speed | 1°/min |
| Step sampling | 0.02° |
| Slit | DS1° RS 0.15 mm SS1° |
| Irradiating angle | 6° |

(2) Infrared Ray Absorption Spectral Analysis.

Measured by using an infrared absorption spectral analyzer, Model A-302, manufactured by Nippon Bunko Co.

(3) Differential Thermal Analysis.

Measured by using a TAS-100-TG8110 manufactured by Rigaku Co. under the measuring conditions of using a standard substance $\alpha\text{-}Al_2O_3$, raising the temperature at a rate of 10° C./min. in the air at 20 to 320° C.

(4) Observation using a Scanning-type Electron Microscope.

Observed by using a scanning electron microscope, S-570, manufactured by Hitachi, Ltd.

(5) Specific Surface Area/porous Volume.

Measured in compliance with the BET method by using Sorptomatic Series 1900 manufactured by Carlo Erba Co.

(6) Average Particle Diameter.

The average particle diameter (median diameter; $\mu$m) was measured by using a laser-diffraction particle size analyzer (Coulter R LS-130) manufactured by Coulter Co.

Example 1

221.58 Grams of zinc oxide of a purity of 99.6% and ion-exchanged water were added into a 2000-ml beaker so that the total volume was 750 ml, and the mixture was stirred and dispersed to prepare a ZnO slurry.

720 Grams of an aluminum sulfate ($Al_2O_3$=7.68%, $SO_3$=18.1%) was gradually poured into the ZnO slurry at room temperature with stirring, and the mixture was messed-up to 1500 ml. Thereafter, the temperature was elevated to 90° C. to conduct the reaction for 5 hours.

After the reaction, the reaction product was filtered, washed with 3000 ml of hot water, dried at 110° C. and was pulverized to obtain a white powder.

The composition of the obtained fine powder was analyzed to be as follows. Properties were as shown in Table 1.

| $Al_{1.00}Zn_{1.44}(OH)_{4.99}(SO_4)_{0.45} \cdot 1.0H_2O$ | |
| --- | --- |
| 2 θ | Relative intensity |
| 11.03° | 100% |
| 21.40° | 32% |
| 34.27° | 45% |
| 60.87° | 26% |

Example 2

A white powder was obtained through the same operation as in Example 1 but changing the reaction time to 25 hours.

The composition of the obtained fine powder was analyzed to be as follows. Properties were as shown in Table 1.

| $Al_{1.00}Zn_{1.48}(OH)_{5.09}(SO_4)_{0.45} \cdot 1.0H_2O$ | |
|---|---|
| 2 θ | Relative intensity |
| 10.73° | 100% |
| 20.63° | 33% |
| 34.13° | 46% |
| 60.93° | 28% |

Example 3

A white powder was obtained through the same operation as in Example 1 but changing the amount of zinc oxide into 265.90 g.

The composition of the obtained fine powder was analyzed to be as follows. Properties were as shown in Table 1.

| $Al_{1.00}Zn_{1.92}(OH)_{5.89}(SO_4)_{0.48} \cdot 0.9H_2O$ | |
|---|---|
| 2 θ | Relative intensity |
| 10.97° | 100% |
| 21.03° | 35% |
| 34.27° | 57% |
| 60.97° | 38% |

An X-ray diffraction image of the polybasic salt is shown in FIG. 9.

Example 4

153.21 Grams of magnesium hydroxide (MgO=64.2%), 22.16 g of zinc oxide of a purity of 99.6%, 14.56 g of ammonium chloride and ion-exchanged water were added into a 2000-ml beaker so that the total volume was 750 ml, and the mixture was stirred and dispersed to prepare a $Mg(OH)_2$—ZnO mixture slurry.

720 Grams of an aluminum sulfate ($Al_2O_3$=7.68%, $SO_3$=18.1%) was gradually poured into the slurry at room temperature with stirring, and the mixture was messed-up to 1500 ml. Thereafter, the temperature was elevated to 90° C. to conduct the reaction for 5 hours.

After the reaction, the reaction product was filtered, washed with 3000 ml of hot water, dried at 110° C. and was pulverized to obtain a white powder.

The composition of the obtained fine powder was analyzed to be as follows. Properties were as shown in Table 1.

| $Al_{1.00}Mg_{0.93}Zn_{0.25}(OH)_{4.68}(SO_4)_{0.34} \cdot 1.3H_2O$ | |
|---|---|
| 2 θ | Relative intensity |
| 10.29° | 100% |
| 20.27° | 58% |
| 35.37° | 24% |
| 61.43° | 28% |

Example 5

136.19 Grams of magnesium hydroxide (MgO=64.2%), 45.20 g of sodium hydroxide of a purity of 96% and ion-exchanged water were added into a 2000-ml beaker so that the total volume was 750 ml, and the mixture was stirred and dispersed to prepare a $Mg(OH)_2$ slurry.

720 Grams of an aluminum sulfate ($Al_2O_3$=7.68%, $SO_3$=18.1%) and 300 g of a zinc sulfate aqueous solution (ZnO=14.7%, $SO_3$=14.5%) were gradually poured into the $Mg((OH)_2$ slurry with stirring, and the mixture was messed-up to 1500 ml. Thereafter, the temperature was elevated to 90° C. to conduct the reaction for 5 hours.

After the reaction, the reaction product was filtered, washed with 3000 ml of hot water, dried at 110° C. and was pulverized to obtain a white powder.

The composition of the obtained fine powder was analyzed to be as follows. Properties were as shown in Table 1.

| $Al_{1.00}Mg_{0.72}Zn_{0.51}(OH)_{4.77}(SO_4)_{0.35} \cdot 1.2H_2O$ | |
|---|---|
| 2 θ | Relative intensity |
| 10.43° | 100% |
| 20.49° | 50% |
| 35.15° | 32% |
| 61.44° | 30% |

Example 6

450 Grams of a zinc sulfate aqueous solution (ZnO=14.7%, $SO_3$=14.5%) and ion-exchanged water were added into a 2000-ml beaker so that the total volume was 1000 ml. While stirring the aqueous solution, an aqueous solution of sodium hydroxide was gradually added thereto until the pH was 7.0, and the reaction was continued for one hour. After the reaction, the reaction product was filtered and washed with 6000 ml of hot water to obtain a $Zn(OH)_2$ cake. The whole amount of the cake was dispersed in the ion-exchanged water in a 2000-ml beaker and to which were further added 119.16 g of magnesium hydroxide (MgO=64.2%) and the ion-exchanged water so that the volume was 750 ml. The mixture was stirred and dispersed to prepare a $Mg(OH)_2$—$Zn(OH)_2$ mixture slurry.

720 Grams of an aluminum sulfate ($Al_2O_3$=7.68%, $SO_3$=18.1%) was gradually poured into the slurry at room temperature with stirring, and the mixture was messed-up to 1500 ml. Thereafter, the temperature was elevated to 90° C. to conduct the reaction for 5 hours.

After the reaction, the reaction product was filtered, washed with 3000 ml of hot water, dried at 110° C. and was pulverized to obtain a white powder.

The composition of the obtained fine powder was analyzed to be as follows. Properties were as shown in Table 1.

| $Al_{1.00}Mg_{0.52}Zn_{0.75}(OH)_{4.77}(SO_4)_{0.37} \cdot 1.2H_2O$ | |
|---|---|
| 2 θ | Relative intensity |
| 10.34° | 100% |
| 20.51° | 49% |
| 34.52° | 31% |
| 61.03° | 27% |

An X-ray diffraction image of the polybasic salt is shown in FIG. 10.

Example 7

1.79 Grams of NaOH was dissolved in 300 ml of ion-exchanged water in a 500-ml beaker. 12.19 Grams of stearic acid was added thereto, and the mixture was heated at 80° C. and was stirred to prepare a sodium stearate solution.

Separately, 10 g of the fine white powder obtained in Example 3 was dispersed in 200 ml of ion-exchanged water. The mixture was added to the above sodium stearate solution and was heated at 90° C. and was stirred for two hours. After the reaction, the reaction product was filtered, washed with 1000 ml of hot water and was dried at 110° C. using a blower-drier overnight.

The composition of the obtained fine powder was analyzed to be as follows. Properties were as shown in Table 1.

| $Al_{1.00}Zn_{1.48}(OH)_{5.09}(C_{18}H_{35}O_2)_{0.43} \cdot 0.4H_2O$ | |
|---|---|
| 2 θ | Relative intensity |
| 2.26° | 22% |
| 3.53° | 62% |
| 5.30° | 61% |
| 21.07° | 100% |
| 34.17° | 45% |
| 60.77° | 33% |

The X-ray diffraction image of the polybasic salt is shown in FIG. 11.

Example 8

15.62 Grams of sodium stearate was dissolved in 300 ml of ion-exchanged water in a 500-ml beaker, and was heated at 80° C. and was stirred to prepare a sodium stearate solution.

Separately, 10 g of the fine white powder obtained in Example 6 was dispersed in 200 ml of ion-exchanged water. The mixture was added to the above sodium stearate solution and was heated at 90° C. and was stirred for two hours. After the reaction, the reaction product was filtered, washed with 1000 ml of hot water and was dried at 110° C. using a blower-drier overnight.

The composition of the obtained fine powder was analyzed to be as follows. Properties were as shown in Table 1.

| $Al_{1.00}Mg_{0.52}Zn_{0.75}(OH)_{4.81}(C_{18}H_{35}O_2)_{0.37} \cdot 0.6H_2O$ | |
|---|---|
| 2 θ | Relative intensity |
| 2.26° | 17% |
| 3.58° | 19% |
| 7.20° | 51% |
| 20.97° | 100% |
| 35.37° | 13% |
| 61.03° | 7% |

Example 9

9.39 Grams of $Na_2HPO_4 \cdot 12H_2O$ (purity of 99%) was introduced into a 500-ml beaker, and to which ion-exchanged water was added to prepare 200 ml of an $Na_2HPO_4$ solution.

Separately, 10 g of the fine white powder obtained in Example 2 was dispersed in 100 ml of ion-exchanged water. The mixture was added to the above $Na_2HPO_4$ solution and was heated at 90° C. and was stirred for two hours. After the reaction, the reaction product was filtered, washed with 1000 ml of hot water, dried at 110° C. for 12 hours, and was pulverized to obtain a fine white powder.

The composition of the obtained fine powder was analyzed to be as follows. Properties were as shown in Table 1.

| $Al_{1.00}Zn_{1.49}(OH)_{5.17}(HPO_4)_{0.41} \cdot 1.0H_2O$ | |
|---|---|
| 2 θ | Relative intensity |
| 8.10° | 68% |
| 15.01° | 78% |
| 22.58° | 100% |
| 34.18° | 79% |
| 61.20° | 63% |

Example 10

A white powder was obtained through the same operation as in Example 9 but using $Na_2HPO_4 \cdot 12H_2O$ (purity, 99%) in an amount of 9.13 g and using the fine white powder obtained in Example 6 instead of the fine white powder obtained in Example 2.

The composition of the obtained fine powder was analyzed to be as follows. Properties were as shown in Table 1.

| $Al_{1.00}Mg_{0.58}Zn_{0.80}(OH)_{5.10}(HPO_4)_{0.33} \cdot 1.2H_2O$ | |
|---|---|
| 2 θ | Relative intensity |
| 8.50° | 43% |
| 14.63° | 43% |
| 22.50° | 100% |
| 35.27° | 85% |
| 61.37° | 77% |

Example 11

19.5 Grams of a sodium silicate solution No. 3 ($SiO_2$=22.0%, $Na_2O$=7.08%) was introduced into a 500-ml beaker, and to which ion-exchanged water was added to prepare 200 ml of a sodium silicate aqueous solution.

Separately, 26.4 g of the reaction product (solid content of 37.9%) after washed obtained in Example 3 was dispersed in 100 ml of ion-exchanged water. The mixture was added to the above sodium silicate solution and was heated at 50° C. and was stirred for two hours. After the reaction, the reaction product was filtered, washed with hot water, dried at 110° C. for 12 hours and was pulverized to obtain a fine white powder.

The composition of the obtained fine powder was analyzed to be as follows. Properties were as shown in Table 1.

| $Al_{1.00}Zn_{1.92}(OH)_{5.89}(SO_4)_{0.18}(Si_3O_7)_{0.30}.1.3H_2O$ | |
|---|---|
| 2 θ | Relative intensity |
| 8.80° | 100% |
| 14.27° | 13% |
| 22.21° | 43% |
| 34.05° | 79% |
| 60.70° | 57% |

Comparative Example 1

Synthesis of a Magaldrate 100.34 Grams of an aluminum sulfate ($Al_2O_3$=7.68%, $SO_3$=18.1%) was added to 1112.4 g of an $Al(OH)_3$ paste ($Al_2O_3$=1.50%), and to which was further added 60.00 g of magnesium hydroxide (MgO=64.2%) with vigorous stirring. And then, the resulting mixture is left quietly for 24 hours to maintain the reaction.

The paste after the reaction was dried at 110° C. and was pulverized to obtain a white powder.

From the X-ray analysis, the obtained fine powder was a mixture of a magaldrate disclosed in Japanese Examined Patent Publication (Kokoku) No. 58210/1990 and an aluminum hydroxide (gibbsite).

FIG. 3 shows an X-ray diffraction image of the magaldrate disclosed in Japanese Examined Patent Publication (Kokoku) No. 58210/1990 and FIG. 4 shows an X-ray diffraction image of a USP-referred standard magaldrate. Since these drawings do not show a scale of angles, the angles refer to values of the Journal of Pharmaceutical Science, Vol. 6, p. 325, 1978.

| 2 θ | Relative intensity |
|---|---|
| 11.42° | 57% |
| 23.22° | 44% |
| 34.91° | 78% |
| 39.16° | 30% |
| 46.07° | 37% |
| 60.95° | 100% |
| 62.32° | 85% |

Comparative Example 2

Synthesis of a Zinc-modified Hydrotalcite 37.0 Grams of NaOH (purity of 96%) and 11.16 g of $Na_2CO_3$ (purity of 99.7%) were added to ion-exchanged water with stirring, and the mixture was heated at 40° C. To this aqueous solution was gradually poured an aqueous solution obtained by adding 45.96 g of $MgCl_2.6H_2O$ (19.73% as MgO), 10.33 g of $ZnCl_2$ (59.12% as ZnO) and 37.33 g of $AlCl_3.6H_2O$ (20.48% as $Al_2O_3$) to 500 ml of ion-exchanged water, such that the molar ratio of $CO_3$/Al was 0.7. The mixture was hydrothermally reacted at 170° C. for 20 hours with stirring.

After the reaction, the reaction product was filtered, washed with 6000 ml of hot water, dried at 110° C. and was pulverized to obtain a white powder.

The composition of the obtained fine powder was analyzed to be as follows. Properties were as shown in Table 1.

| $Al_6Mg_{1.5}Zn_{0.5}(OH)_{16}(CO_3).nH_2O$ | |
|---|---|
| 2 θ | Relative intensity |
| 11.67° | 100% |
| 23.47° | 59% |
| 34.82° | 15% |
| 39.42° | 9% |
| 46.89° | 8% |
| 60.96° | 10% |
| 62.03° | 11% |

An X-ray diffraction image of the hydrotalcite is shown in FIG. 6.

Comparative Example 3

Synthesis of a Lithium Aluminum Composite Hydroxide 25.00 Grams of sodium hydroxide (NaOH content of 96%) and 7.44 g of sodium carbonate ($Na_2CO_3$ content of 99.7%) were added to 2 liters of distilled water with stirring, and the mixture was heated at 40° C. Then, to this solution was gradually added an aqueous solution which was obtained by adding 4.33 g of lithium chloride (52.90% as $Li_2O$) and 49.78 g of aluminum chloride (20.48% as $Al_2O_3$) to 500 ml of distilled water such that the molar ratio of Al/Li was 2.0. The reaction was conducted with stirring at a temperature of 90° C. for 20 hours. The obtained reaction suspension was filtered, washed with water, dried at 70° C. and was, then, pulverized using a small sample mill to obtain a white powder.

The composition of the obtained fine powder was analyzed to be as follows. Properties were as shown in Table 1.

| $Li_2Al_4(OH)_{12}CO_3.nH_2O$ | |
|---|---|
| 2 θ | Relative intensity |
| 11.77° | 100% |
| 20.20° | 11% |
| 23.61° | 59% |
| 36.07° | 29% |
| 40.63° | 14% |
| 48.03° | 18% |
| 63.23° | 11% |
| 64.53° | 9% |

An X-ray diffraction image of the salt of lithium aluminum composite hydroxide is shown in FIG. 7.

TABLE 1

| | Laminate asymmetric indexes Is | Degree of orientation Io | Specific surface area (m²/g) | Porous volume (ml/g) | Average particle diameter (μm) | (a + b)/x | y/(a + b+ x) | b/(a + b) |
|---|---|---|---|---|---|---|---|---|
| Example No. | | | | | | | | |
| 1 | 3.57 | 3.80 | 5.50 | 0.025 | 6.2 | 1.44 | 2.05 | 1.00 |
| 2 | 2.73 | 3.55 | 6.02 | 0.029 | 6.2 | 1.48 | 2.05 | 1.00 |
| 3 | 2.35 | 2.67 | 4.90 | 0.025 | 5.2 | 1.92 | 2.02 | 1.00 |
| 4 | 4.40 | 3.54 | 3.91 | 0.020 | 4.3 | 1.18 | 2.15 | 0.21 |
| 5 | 5.36 | 3.29 | 3.84 | 0.027 | 4.6 | 1.23 | 2.14 | 0.41 |
| 6 | 10.42 | 3.76 | 4.70 | 0.031 | 4.9 | 1.27 | 2.12 | 0.59 |
| 7 | 7.18 | | | | 3.1 | 1.92 | 2.02 | 1.00 |
| 8 | 1.69 | | | | 3.0 | 1.27 | 2.12 | 0.59 |
| 9 | 3.85 | | | | 4.8 | 1.49 | 2.08 | 1.00 |
| 10 | 7.83 | | 146 | 0.425 | 4.2 | 1.38 | 2.14 | 0.58 |
| 11 | 3.79 | | | | 4.1 | 1.92 | 2.02 | 1.00 |
| Comparative Example No. | | | | | | | | |
| 1 | 1.36 | 0.57 | | | | — | — | — |
| 2 | — | — | | | | 3.00 | 2.00 | 0.25 |
| 3 | — | — | | | | 0.25 | 2.00 | — | a, b, x, y and z are indexes of $M^2{}_aZn_bM^3{}_x(OH)_y(A)_z \cdot nH_2O$.

According to the present invention, it is made possible to obtain a composite metal polybasic salt having a chemical composition represented by the following general formula (1), $$M^2{}_aZn_bM^3{}_x(OH)_y(A)_z \cdot nH_2O \quad (1)$$

wherein $M^2$ is a divalent metal other than Zn, $M^3$ is a trivalent metal, A is an inorganic or organic anion, and a, b, x, y and z are numbers satisfying the following formulas, $0 \leq a$, $0 < b$ $3x+2(a+b)-y-mz=0$ (wherein m is a valency of anion A), $0.3 \leq (a+b)/x \leq 2.5$, $1.5 \leq y/(x+a+b) \leq 3.0$, and $4.0 \leq (x+a+b)/z \leq 20.0$, and n is a number of not larger than 7, exhibiting diffraction peaks at $2\theta = 2$ to $15°$, $2\theta = 19.5$ to $24°$ and $2\theta = 33$ to $50°$, and a single peak at $2\theta = 60$ to $64°$ and, more preferably, a single peak at $2\theta = 33$ to $50°$ in the X-ray diffraction (Cu-α). The zinc-modified composite metal polybasic salt is useful as an additive for resins, as a heat-insulating agent and as an anion-exchanger.

What is claimed is:

1. A composite metal polybasic salt having a chemical composition represented by the following general formula (1), $$Mg_aZn_bM^3{}_x(OH)_y(A)_z \cdot nH_2O \quad (1)$$

wherein $M^3$ is a trivalent metal, A is a sulfuric acid ion, and a, b, x, y and z are numbers satisfying the following formulas, i) $0 \leq a$, $0 < b$ ii) $3x+2(a+b)-y-mz=0$ (wherein m is a valency of anion A), iii) $0.3 \leq (a+b)/x \leq 2.5$, iv) $1.5 \leq y/(x+a+b) \leq 3.0$, and v) $4.0 \leq (x+a+b)/z \leq 20.0$, and n is a number of not larger than 7, exhibiting diffraction peaks at $2\theta = 2$ to $15°$, $2\theta = 19.5$ to $24°$, a single peak at $2\theta = 33$ to $50°$, and a single peak at $2\theta = 60$ to $64°$ in the X-ray diffraction (Cu-α).

2. A composite metal polybasic salt according to claim 1, wherein the trivalent metal ($M^3$) in said formula is aluminum.

3. A composite metal polybasic salt according to claim 1, which has a laminate asymmetric index (Is) defined by the following formula (2), $$Is = \tan\theta_2 / \tan\theta_1 \quad (2)$$

wherein $\theta_1$ is an angle subtended by a peak perpendicular in the X-ray diffraction peak of a predetermined spacing and a peak tangent on the narrow angle side, and $\theta_2$ is an angle subtended by the peak perpendicular at the above peak and a peak tangent on the wide angle side, which is not smaller than 1.5 at a peak of $2\theta = 33$ to $50°$.

4. An additive for resins comprising a composite metal polybasic salt according to claim 1.

5. A heat insulator comprising a composite metal polybasic salt according to claim 1.

6. An anion exchanger comprising a composite metal polybasic salt according to claim 1.

7. A composite metal polybasic salt obtained by ion-exchanging the sulfuric acid anion in the composite metal polybasic salt of claim 1 with at least one anion selected from the group consisting of a carbonic acid ion, silicic acid ion, an organopolycarboxylic acid ion and a phosphoric acid ion.

8. An additive for resins comprising a composite metal polybasic salt according to claim 7.

9. A heat insulator comprising a composite metal polybasic salt according to claim 7.

10. A method of preparing the composite metal polybasic salt of claim 1 by reacting a sulfuric acid salt of a trivalent metal with an oxide, a hydroxide or a sulfuric acid salt of zinc an oxide, a hydroxide or a sulfuric acid salt of and magnesium, under the conditions of a pH of from 3.8 to 9.0 and a temperature of not lower than 50° C.

11. A method of preparing the composite metal polybasic salt of claim 7 by executing the ion-exchange of the sulfuric acid anion of the composite metal polybasic salt of claim 1 in the presence of at least one acid selected from the group consisting of a carbonic acid, a silicic acid, an organocarboxylic acid and a phosphoric acid, or a soluble salt thereof.

* * * * *